(12) United States Patent
Fritz-Langhals et al.

(10) Patent No.: US 12,145,937 B2
(45) Date of Patent: Nov. 19, 2024

(54) PROCESS FOR PREPARING BICYCLIC GUANIDINES

(71) Applicant: WACKER CHEMIE AG, Munich (DE)

(72) Inventors: Elke Fritz-Langhals, Ottobrunn (DE); Uwe Scheim, Coswig (DE)

(73) Assignee: WACKER CHEMIE AG, Munich (DE)

( * ) Notice: Subject to any disclaimer, the term of this patent is extended or adjusted under 35 U.S.C. 154(b) by 834 days.

(21) Appl. No.: 17/272,898

(22) PCT Filed: Sep. 6, 2018

(86) PCT No.: PCT/EP2018/074069
§ 371 (c)(1),
(2) Date: Mar. 2, 2021

(87) PCT Pub. No.: WO2020/048604
PCT Pub. Date: Mar. 12, 2020

(65) Prior Publication Data
US 2021/0214367 A1    Jul. 15, 2021

(51) Int. Cl.
*C07D 487/04* (2006.01)

(52) U.S. Cl.
CPC .................. *C07D 487/04* (2013.01)

(58) Field of Classification Search
CPC .................................. C07D 487/04
USPC ........................................ 544/279
See application file for complete search history.

(56) References Cited

U.S. PATENT DOCUMENTS

| | | |
|---|---|---|
| 4,797,487 A | 1/1989 | A'Court |
| 2009/0281313 A1 | 11/2009 | Minch et al. |
| 2009/0281314 A1 | 11/2009 | Boyd et al. |
| 2012/0220770 A1 | 8/2012 | Hickenboth et al. |
| 2012/0259112 A1 | 10/2012 | Gridnev |
| 2013/0163130 A1 | 6/2013 | Yamada et al. |
| 2013/0289272 A1 | 10/2013 | Dacko et al. |
| 2017/0210856 A1 | 7/2017 | Wacker |
| 2018/0194902 A1 | 7/2018 | Prasse et al. |

FOREIGN PATENT DOCUMENTS

| | | |
|---|---|---|
| DE | 102015216598 A1 | 3/2017 |
| EP | 3172178 B1 | 9/2018 |
| JP | 2017521538 A | 8/2007 |
| JP | 2010106195 A | 5/2010 |

OTHER PUBLICATIONS

Aldrich, 1998-1999, p. 1593 (Year: 1998).*
Tozawa et al., "An Efficient Method for the Preparation of Carboxamides by Dehydration Condensation Using Tetrakis (1,1,1,3,3,3-hexafluoro-2-propoxy)silane" Chemistry Letter, (2005) 34 (12) pp. 1586-1587.

* cited by examiner

*Primary Examiner* — Taylor V Oh
(74) *Attorney, Agent, or Firm* — BROOKS KUSHMAN P.C.

(57) ABSTRACT

Bicyclic guanidines are prepared by reacting dialkylenetriamines with dialkylcarbonates in the presence of a silane of the formula $$\mathrm{Si(OR^{x})_{o}R^{y}{}_{(4-o)}} \qquad \text{(IV)}$$

and/or their partial hydrolysates, with the proviso that contain minimally one unit $R^x$ which is monovalent optionally substituted hydrocarbon radial with 3 to 10 carbon atoms.

13 Claims, No Drawings

PROCESS FOR PREPARING BICYCLIC GUANIDINES

CROSS REFERENCE TO RELATED APPLICATIONS

This application is the U.S. National Phase of PCT Appln. No. PCT/EP2018/074069 filed Sep. 6, 2018, the disclosure of which is incorporated in its entirety by reference herein.

BACKGROUND OF THE INVENTION

1. Field of the Invention

The invention relates to a process for producing bicyclic guanidines and formulations containing bicyclic guanidines and to the use thereof as a catalyst.

2. Description of the Related Art

Bases are used as catalysts in numerous industrial chemical processes. Organic bases are particularly preferred in the field of polymer chemistry because they are much more soluble in nonpolar media than inorganic bases such as for example sodium hydroxide or potassium hydroxide, which can also cause undesired side reactions.

For the greatest possible catalytic effect, a high base strength is desirable. Bicyclic guanidines such as for example 1,5,7-triazabicyclo[4.4.0]-dec-5-ene (TBD) are accordingly preferred in principle over the more common, but considerably less strongly basic compounds tetramethylguanidine, DBU (diazabicycloundecene) or DBN (diazabicyclodecene).

TBD is, for example, a highly effective catalyst for the ring-opening polymerization of lactones and cyclic siloxanes and also in the production of polyurethanes. According to DE 10 2015216 598 A1, the endcapping of hydroxypolysiloxanes can be catalyzed efficiently with TBD.

The industrial use of TBD and other bicyclic guanidines has however been hindered up to now by their lack of industrial accessibility. TBD can, for example, be prepared by reacting dipropylenetriamine with the C1 building blocks carbon disulfide, carbodiimides, and guanidines. However, the carbon disulfide route described in U.S. Pat. No. 4,797,487 results in the formation of toxic hydrogen sulfide gas and minimizing the risk of its inadvertent release represents a substantial technical challenge. A further safety risk is the low flash point of carbon disulfide.

The routes described in US 20130289272 and US 2013163130 starting from carbodiimides are uneconomical on account of the high cost of diimides. In addition, impurities can be separated only with great difficulty.

In the synthesis of bicyclic guanidines using acyclic guanidine salts as C1 building blocks described by way of example in US 2012/0259112, large amounts of ammonia are produced that must be captured and disposed of, which likewise makes the process considerably more costly. Moreover, TBD is obtained as a salt, which has to be converted into the free base in an additional step.

The publications US 2009/0281313 and US 2009/0281314 describe the production of TBD from dipropylenetriamine with dimethyl carbonate. This route has the advantage over the routes mentioned above that inexpensive, industrially available starting materials can be used and that no toxic gases are produced in the reaction. The reaction proceeds via the initial formation of a cyclic urea with double elimination of methanol and, at temperatures of >200° C. and reaction times of up to 50 hours, the formation of TBD, the preferred reaction medium used for this being high-boiling ethers, for example glycol ethers such as triethylene glycol dimethyl ether and diethylene glycol monobutyl ether or glycol ether acetals such as butyl carbitol formal. These allow the reaction to be carried out without pressure, even at high temperatures of >200° C. The product TBD is isolated after the reaction as a solid, either by removing the solvent, the product TBD being present in the residue, or by crystallizing the product out through addition of a precipitant, for example a hydrocarbon. In further embodiments, the reaction mixture in the high-boiling ether is additionally mixed with a reagent for binding the water formed, examples of these being disilazanes and tetraethoxysilane (TEOS). However, US 2009/0281314 section discloses that the use of TEOS under the conditions specified therein results in the formation of insoluble silica, which can be removed only by filtration of the diluted product solution, which increases process costs further. Moreover, the use of glycol ethers as solvents is problematic, since they tend to form thermally unstable ether peroxides on contact with air and are also toxic. These solvents must therefore be removed as completely as possible before use, which necessitates repeated recrystallization. This makes the manufacture of the product considerably more costly and the use thereof ultimately uneconomical.

Crystalline bicyclic guanidine is not very suitable particularly for applications in polymer chemistry, since it dissolves only very slowly in polymers, particularly in siloxanes. The protracted dissolution process adds considerably to the technical challenges, which can ultimately make the process uneconomical. There is also always the risk that insoluble catalyst constituents will remain in the reaction mixture, resulting in increased consumption, which in turn lowers economic viability.

The object was therefore to provide a process for producing bicyclic guanidines that does not have the abovementioned disadvantages and allows inexpensive and technically simple production. A further object is to provide a liquid formulation of bicyclic guanidine that can be produced inexpensively in a simple manner and can be used directly for catalytic purposes.

SUMMARY OF THE INVENTION

The invention provides a process for producing bicyclic guanidines by reacting (A) dialkylenetriamine with (B) dialkyl carbonate
in the presence of (C) silane of the formula $$\mathrm{Si(OR^{x})_{o}R^{y}_{(4-o)}} \qquad (IV)$$

and/or partial hydrolysates thereof,
where
$R^x$ may be identical or different and are monovalent, optionally substituted hydrocarbon radicals having 2 to 10 carbon atoms,
$R^y$ may be identical or different and are monovalent, optionally substituted hydrocarbon radicals having 1 to 30 carbon atoms in which individual $CH_2$ moieties not bonded to silicon may be replaced by oxygen or substituted by silyl groups and
is 1, 2, 3 or 4, preferably 2, 3 or 4, more preferably 3, with the proviso that, in the case of silanes of the formula (IV) where o=4, at least two radicals $R^x$ represent a monovalent, optionally substituted hydrocarbon radical having 3 to 10 carbon atoms.

DETAILED DESCRIPTION OF THE PREFERRED EMBODIMENTS

The dialkylenetriamine (A) used according to the invention is preferably one of the general formula

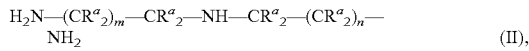

$$H_2N-(CR^a{}_2)_m-CR^a{}_2-NH-CR^a{}_2-(CR^a{}_2)_n-NH_2 \qquad (II),$$

where
- m and n are independently 1, 2, 3 or 4, preferably 1, 2 or 3, more preferably 1 or 2 and
- $R^a$ may be identical or different and is a hydrogen atom or monovalent hydrocarbon radicals in which individual methylene groups may be replaced by oxygen or by —NH— or —$NR^d$-moieties, where $R^d$ represents monovalent, optionally substituted hydrocarbon radicals having 2 to 10 carbon atoms.

Examples of monovalent $R^a$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical, the 2-methylpentyl radical; heptyl radicals such as the n-heptyl radical; octyl radicals such as the n-octyl radical, and isooctyl radicals such as the 2,2,4-trimethylpentyl radical; nonyl radicals such as the n-nonyl radical; decyl radicals such as the n-decyl radical; undecyl radicals such as the n-undecyl radical, dodecyl radicals such as the n-dodecyl radical; octadecyl radicals such as the n-octadecyl radical; cycloalkyl radicals such as the cyclopentyl, cyclohexyl, cycloheptyl, and methylcyclohexyl radicals; alkenyl radicals such as the vinyl, 1-propenyl, and 2-propenyl radicals; aryl radicals such as the phenyl, naphthyl, anthryl, and phenanthryl radical, alkaryl radicals such as o, m, p-tolyl radicals; xylyl radicals and ethylphenyl radicals; and aralkyl radicals such as the benzyl radical, and the α- and β-phenylethyl radical, and —OH, —$OCH_3$, —$OC_2H_5$, —$CH_2$—O—$CH_3$, —$NH_2$, —$CH_2$—$NH_2$ or —$CH_2$—$N(CH_3)_2$.

The radicals $R^a$ are preferably hydrogen or hydrocarbon radicals having 1 to 10 carbon atoms in which individual methylene groups may be replaced by oxygen or by —NH— or —$NR^d$— moieties, where $R^d$ is as defined above, more preferably hydrogen or aliphatic, linear or branched hydrocarbon radicals having 1 to 6 carbon atoms, in particular hydrogen.

In the triamine (A) of the formula (II), m and n are preferably the same, m=n=1 or 2 being particularly preferred.

The triamine (A) used according to the invention is preferably bis(3-aminopropyl)amine, bis(2-aminoethyl) amine, 1-amino-3-[(3-amino-2-hydroxypropyl)amino]propan-2-ol or N-(2-aminoethyl)-N-(3-aminopropyl)amine, more preferably bis(3-aminopropyl)amine.

The dialkyl carbonate (B) used according to the invention is preferably one of the general formula

$$R^bO-CO-OR^b \qquad (III),$$

where
- $R^b$ are identical or different and are mono- or divalent, aliphatically saturated hydrocarbon radicals.

When $R^b$ represents divalent, aliphatically saturated hydrocarbon radicals, these are preferably linked to one another, forming a ring via the two oxygen atoms.

Examples of radicals $R^b$ are the examples stated for radical $R^a$ for monovalent, aliphatically saturated hydrocarbon radicals and divalent aliphatic hydrocarbon radicals such as —$CH_2$—$(CH_2)_p$—$CH_2$—, where p is preferably equal to 0, 1, 2, 3 or 4, more preferably 0 or 1, where the divalent radicals $R^b$ are preferably linked to one another, forming a ring via the two oxygen atoms.

The radicals $R^b$ are preferably mono- or divalent, aliphatically saturated hydrocarbon radicals having 1 to 10 carbon atoms, more preferably mono- or divalent, aliphatically saturated linear or branched hydrocarbon radicals having 1 to 6 carbon atoms, in particular the methyl, ethyl, propyl, ethylene or propylene radicals, most preferably the methyl or ethyl radicals.

The carbonate (B) used according to the invention is preferably dimethyl carbonate, diethyl carbonate, di-n-propyl carbonate, ethylene carbonate or propylene carbonate, more preferably dimethyl carbonate or diethyl carbonate.

In the process according to the invention, dialkyl carbonate (B) is preferably used in molar amounts of 0.5 to 2.0 mol, more preferably 0.8 to 1.5 mol, in each case based on 1 mol of the dialkylenetriamine (A) used.

The radicals $R^x$ are preferably linear, branched or cyclic, saturated or unsaturated hydrocarbon radicals having 2 to 6 carbon atoms, more preferably aliphatically saturated linear or branched hydrocarbon radicals having 2 to 6 carbon atoms, in particular the ethyl, n-propyl, i-propyl, n-butyl or 2-butyl radicals, most preferably the ethyl radical.

Examples of radicals $R^y$ are the examples stated for radical $R^a$.

The radicals $R^y$ are preferably linear, branched or cyclic saturated or unsaturated hydrocarbon radicals having 1 to 20 carbon atoms, more preferably aliphatic, linear or branched hydrocarbon radicals having 1 to 12 carbon atoms.

Examples of silanes (C) used according to the invention are i-octyl-Si(OEt)$_3$, methyltriethoxysilane, ethyltriethoxysilane, vinyltriethoxysilane, propyltriethoxysilane, butyltriethoxysilane, cyclohexyltriethoxysilane, 2-methylpropyltriethoxysilane, pentyltriethoxysilane, methyltris(1-methylethoxy)silane, n-octyltriethoxysilane, phenyltriethoxysilane, benzyltriethoxysilane, Si(O-2-butyl)$_4$, Si(OEt)(O-2-butyl)$_3$, Si(OEt)$_2$(O-2-butyl)$_2$, Si(O-i-Prop)$_4$, Si(OEt)(O-i-Prop)$_3$, Si(OEt)$_2$(O-i-Prop)$_2$, and (EtO)$_3$Si—$CH_2$—$CH_2$—Si(OEt)$_3$, (EtO)$_3$Si—$CH_2$—$CH_2$—SiMe$_3$, (EtO)$_2$MeSi—$CH_2$—$CH_2$—SiMe(OEt)$_2$, and the partial hydrolysates thereof, where Et represents equally the ethyl radical and Prop equally the propyl radical.

The silanes (C) used according to the invention are preferably ones in which o=3 and $R^x$ is a monovalent, aliphatically saturated, linear or branched alkyl radical having 2 to 4 carbon atoms and $R^y$ is a monovalent, aliphatic, linear or branched hydrocarbon radical having 6 to 10 carbon atoms or one in which o=4 and at least two radicals $R^x$ is a monovalent, aliphatically saturated, linear or branched hydrocarbon radical having 3 to 8 carbon atoms and/or the partial hydrolysates thereof.

The silanes (C) used according to the invention are more preferably i-octyl-Si(OEt)$_3$, n-heptyl-Si(OEt)$_3$, n-decyl-Si(OEt)$_3$, phenyl-Si(OEt)$_3$, Si(O-2-butyl)$_4$, Si(OEt)(O-2-butyl)$_3$, Si(OEt)$_2$(O-2-butyl)$_2$, Si(O-i-Prop)$_4$, Si(OEt)(O-i-Prop)$_3$ or Si(OEt)$_2$(O-i-Prop)$_2$, and/or the partial hydrolysates thereof, in particular i-octyl-Si(OEt)$_3$ and/or the partial hydrolysates thereof.

When component (C) is a partial hydrolysate of silanes of the formula (IV), those having 2 to 5 silicon atoms are preferred.

In the process according to the invention, component (C) is preferably used in amounts of 30 to 1000 parts by weight, more preferably 100 to 500 parts by weight, in each case based on 100 parts by weight of dialkylenetriamine (A).

In the process according to the invention, in addition to components (A), (B), and (C), further substances may be used that are in each case different from components (A), (B), and (C), for example bases (D) or organic solvents (E).

Examples of optionally used bases (D) are inorganic or organic bases.

The bases (D) that may optionally be used are preferably nitrogen bases that are different from component (A), more preferably TBD, DBU, DBN, pyridine or dimethylaminopyridine, guanidine, tetramethylguanidine or tetraethylguanidine.

When bases (D) are used in the process according to the invention, the amounts used are preferably 0.01 to 20 parts by weight, more preferably 0.1 to 10 parts by weight, and in particular 1 to 5 parts by weight, in each case based on 100 parts by weight of dialkylenetriamine (A) used. In the process according to the invention, preference is given to using no base (D).

The solvents (E) that may optionally be used are preferably alcohols, phenols, nitriles, dialkyl ethers, diaryl ethers or hydrocarbons, preference being given to alcohols or hydrocarbons and particular preference to alcohols.

When solvents (E) are used in the process of the invention, the amounts used are preferably 0.1 to 200 parts by weight, more preferably 1 to 100 parts by weight, and in particular 10 to 50 parts by weight, in each case based on 100 parts by weight of dialkylenetriamine (A) used. In the process according to the invention, preference is given to using no solvent (E).

If desired, further substances may also be used in the process according to the invention, for example the fillers (f), colorants (g), and polymers (h) described below in connection with the preparation according to the invention, but this is not preferable.

Glycol ethers are preferably not used in the process according to the invention.

In the process according to the invention, preference is given to using no further constituents over and above components (A) to (E) and (f), (g), and (h), more preferably no further constituents over and above components (A) to (E).

The components used in the process according to the invention may in each case be a single type of such a component or may be a mixture of at least two types of a respective component.

In the process according to the invention, it is preferable when components (A) and (B) and optionally components (D), (E), (f), (g), and (h) are mixed and allowed to react in a first step, which is followed by a second step in which component (C) and optionally components (D), (E), (f), (g) and (h) are added and the mixture is heated to a temperature greater than 200° C.

In the first step of the process according to the invention, component (A) and optionally components (D), (E), (f), (g), and (h) are initially charged, preferably at temperatures between room temperature and 120° C., and component (B) is added, wherein an exothermic reaction takes place that results in a further rise in the temperature of the reaction mixture. The temperature is preferably held at 20 to 120° C., optionally by cooling or heating, with removal of the alcohol formed, preferably $R^b$—OH, preferably by distillation. The alcohol formed may also be removed after the reaction, preferably by distillation. In this reaction, the elimination of alcohol results in the formation of a cyclic urea.

In the second step of the process according to the invention, component (C) and optionally components (D), (E), (f), (g), and (h) are added to the reaction mixture obtained in the first step and heated to a temperature preferably of 200° C. to 280° C., more preferably of 210° C. to 260° C., in particular to a temperature of 220° C. to 250° C., and allowed to react, resulting in the formation of alcohol $R^x$—OH, which is preferably removed. The alcohol is removed preferably by distillation, more preferably at pressures between 0.1 mbar and 50 bar, particularly preferably at pressures between 1 mbar and 20 bar, most preferably at ambient pressure.

In a further embodiment of the process according to the invention, all components are mixed with one another in any desired order and allowed to react; once the exothermic reaction has subsided, the temperature is increased to 220-280° C. over a period of preferably 0.1 to 10 hours, more preferably 1 to 5 hours, and held within this temperature range for preferably 5 to 30 hours, more preferably 8 to 20 hours.

The process according to the invention is preferably carried out under an inert gas, such as for example nitrogen.

The process according to the invention may be carried out continuously, batchwise or semi-continuously, with preference given to a batchwise process.

After the reaction according to the invention, a pale yellow reaction mixture is obtained from which the bicyclic guanidine precipitates in crystalline form almost quantitatively at ambient temperature and can accordingly be separated off in a simple manner, for example by filtration. However, it is also possible to isolate the bicyclic guanidine by fractional distillation, sublimation or solid distillation. The formation of insoluble components such as for example silica preferably does not occur in the process according to the invention.

In the process according to the invention, preference is given to obtaining bicyclic guanidines of the formula (I)

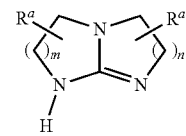

in which $R^a$, m, and n are as defined above.

In the process according to the invention, the separated alcohols, preferably $R^b$—OH and $R^x$—OH, may be reused, for example in the production of alkoxysilanes or in the production of the preparation according to the invention as component (c). If this is done, the process according to the invention does not give rise to any waste products, which represents a particular advantage of the process according to the invention.

In a preferred embodiment, the reaction mixture obtained is at the end of the reaction mixed with water or with a monohydric or polyhydric alcohol. Advantageously, this allows workup of the reaction mixture to be dispensed with altogether, allowing the preparation thus obtained to be used directly.

The invention therefore also provides a preparation consisting of
  (a) bicyclic guanidine,
  (b) silane of the general formula (IV) and/or the partial hydrolysates thereof,
  (c) compound $R^cOH$, wherein $R^c$ is a hydrogen atom or monovalent, optionally substituted hydrocarbon radicals having 1 to 30 carbon atoms, which may be interrupted by oxygen, optionally (d) reaction side products, optionally (e) organic solvents free of hydroxyl groups attached to aliphatic carbon atoms, optionally (f) fillers, optionally (g) colorants, and optionally (h) polymers.

In addition to components (a), (b), and (c) and optionally (e), (f), and (h), the preparations according to the invention may contain reaction side products (d) from the reaction of (A) with (B) according to the invention, which are present preferably when the reaction mixture obtained by the process according to the invention is used without workup to produce the preparations according to the invention, which is preferred.

Component (a) used according to the invention is preferably a compound of the formula (I), more preferably TBD.

The content of bicyclic guanidines (a) in the preparations according to the invention is preferably 2% to 35% by weight, more preferably 5% to 25% by weight.

Component (b) used according to the invention is preferably a silane of the formula (IV) in a mixture with the siloxanes thereof that are formed by hydrolysis and condensation.

The content of silanes and/or siloxanes (b) in the preparations according to the invention is preferably 20% to 90% by weight, more preferably 30% to 70% by weight.

Examples of radical $R^c$ are the radicals stated above for radical $R^y$.

The radical $R^c$ is preferably a hydrogen atom or an aliphatically saturated or aliphatically unsaturated, linear or branched or cyclic, optionally substituted hydrocarbon radical having 1 to 12 carbon atoms, which may be interrupted with oxygen, more preferably aliphatically saturated or aliphatically unsaturated, linear or branched hydrocarbon radicals, optionally substituted by hydroxyl groups, having 1 to 6 carbon atoms, which may be interrupted by oxygen atoms, in particular a hydrogen atom, methyl, ethyl, 2-hydroxyethyl, n-propyl, i-propyl, 2-hydroxypropyl, 2,3-dihydroxypropyl, n-butyl or 2-butyl radical.

Component (c) is preferably water, methanol, ethanol, n-propanol, i-propanol, glycerol, ethylene glycol or propylene glycol, more preferably ethanol.

The content of component (c) in the preparations according to the invention is preferably 5% to 50% by weight, more preferably 10% to 30% by weight.

The proportion by weight of components (a), (b), (c), and optionally (d) in the compositions according to the invention is preferably at least 80% by weight, more preferably at least 90% by weight, in particular 100% by weight.

When the preparations according to the invention contain reaction side products (d), these are present in amounts of preferably 1 to 20 parts by weight, more preferably 2 to 10 parts by weight, in each case based on 100 parts by weight of the total weight of components (a), (b), and (c).

Examples of optionally used component (e) are the examples stated above for organic solvents (E), aside from alcohols.

When the preparations according to the invention contain organic solvents (e), these are present in amounts of preferably 0.01 to 100 parts by weight, more preferably 0.1 to 50 parts by weight, and in particular 1 to 10 parts by weight, in each case based on 100 parts by weight of the total weight of components (a), (b), and (c). The preparations according to the invention preferably contain no organic solvent (e).

Examples of fillers (f) that may optionally be used are non-reinforcing fillers, that is to say fillers having a BET surface area of up to 50 m2/g, such as quartz, diatomaceous earth, calcium silicate, zeolites, silicon nitride, silicon carbide, boron nitride, glass powder; reinforcing fillers, that is to say fillers having a BET surface area of at least 50 m2/g, such as fumed silica, precipitated silica, and silicon-aluminum mixed oxides having a large BET surface area, with preference given to precipitated and fumed silica and particular preference to fumed silica.

When the preparations according to the invention contain fillers (f), these are preferably present in amounts of 0.1 to 100 parts by weight, more preferably 1 to 50 parts by weight, in particular 5 to 20 parts by weight, in each case based on 100 parts by weight of the total weight of components (a), (b), and (c). The preparations according to the invention preferably contain no organic filler (f).

Examples of colorants (g) that may optionally be used are dyes such as phthalocyanines, indanthrene dyes, azo dyes, optical brighteners, and fluorescent dyes, and also pigments such as carbon black or titanium dioxide, with preference given to optical brighteners and carbon black and particular preference to optical brighteners.

When the preparations according to the invention contain colorants (g), these are preferably present in amounts of 0.0001 to 20 parts by weight, more preferably 0.001 to 5 parts by weight, in particular 0.01 to 1 parts by weight, in each case based on 100 parts by weight of the total weight of components (a), (b), and (c). The preparations according to the invention preferably contain no colorants (g).

Examples of polymers (h) that may optionally be used are polysiloxanes, polyethers, polyurethanes or polyureas that are free of organyloxy groups and have preferably 15 to 1000 repeat units, preferably polysiloxanes or polyethers that are free of organyloxy groups, more preferably polysiloxanes free of organyloxy groups.

When the preparations according to the invention contain polymers (h), these are preferably present in amounts of 0.1 to 500 parts by weight, more preferably 1 to 100 parts by weight, and in particular 5 to 50 parts by weight, in each case based on 100 parts by weight of the total weight of components (a), (b), and (c). The preparations according to the invention preferably contain no polymers (h).

The components present in the preparations according to the invention may in each case be a single type of such a component or may be a mixture of at least two types of a respective component.

The preparations according to the invention may be produced by any known process, for example by simple mixing of the individual components. The reaction mixture obtained by the process according to the invention, which consists essentially of (a) bicyclic guanidine and (b) silane of the general formula (IV) and/or the partial hydrolysates thereof, and (d) reaction side products, is preferably mixed with alcohol (c) and optionally with components (e) to (h). This mixing is preferably carried out at a temperature of 10 to 100° C. and at ambient pressure, that is to say about 900 to 1100 hPa.

A subject matter of the present invention further provides a process for producing the preparations according to the invention by mixing the individual components in any desired order.

At 20° C. and 1013 hPa, the preparations according to the invention are preferably almost colorless to slightly yellowish and homogeneous liquids.

The bicyclic guanidines produced according to the invention and the preparations according to the invention may be used wherever bicyclic guanidines have also been used up to now, in particular as a liquid catalyst preparation in the reaction of hydroxysiloxanes with alkoxysilanes ("endcapping"), in the ring-opening polymerization of lactones, lactams, and cyclic carbonates, for the conversion of esters into amides and carbonates into ureas, for aldol condensation, and for the transalkoxylation of alkoxysilanes and alkoxysiloxanes.

The process according to the invention has the advantage that bicyclic guanidines can be prepared in high yields when alkoxysilanes serve simultaneously as the reaction medium and as an agent for the removal of water.

A further advantage of the process according to the invention is that the use of glycol ethers as solvents, which are chemically and toxicologically problematic, can be dispensed with altogether.

Unlike processes of the prior art, in which dark-colored reaction mixtures are obtained, the process surprisingly affords pale yellow reaction mixtures.

The process according to the invention has the further advantage that the alcohol formed by the reaction with water is carried out of the reaction mixture by the alkoxysilanes used surprisingly readily, thereby promoting the process by which the cyclic guanidines are formed.

A further surprise is that the product mixture, which contains cyclic guanidines and alkoxysilane and also the condensation products of the alkoxysilane that are formed by the reaction with water, can be made liquid by adding relatively small amounts of alcohol and that the preparation obtained can accordingly be used directly for catalytic processes without further workup of the reaction mixture.

The preparations according to the invention have the advantage that they are liquid and outstandingly well suited for use as catalysts. In particular, the siloxane content in the formulations according to the invention gives rise to very good miscibility with siloxanes, making catalytic applications in this field particularly advantageous.

A further economic advantage is that the production according to the invention of bicyclic guanidines and the further processing to the liquid formulation according to the invention is carried out without solids being handled and also without needing to remove any waste products.

In the examples that follow, all parts and percentages are by weight unless otherwise stated. Unless otherwise stated, the examples that follow are executed at ambient pressure, i.e. at about 1000 hPa, and at room temperature, i.e. about 20° C. or at a temperature attained on combining the reactants at room temperature without additional heating or cooling. All viscosities stated in the examples should relate to a temperature of 25° C. All experiments are carried out with nitrogen inertization.

Example 1

409 g (3.11 mol) of bis(3-aminopropyl)amine and 11 g of a TBD solution in ethanol having a TDB content of approx. 19% were mixed at room temperature and 293 g (3.24 mol) of dimethyl carbonate was added over a period of one hour, with stirring. A temperature rise in bottoms temperature to 90° C. was observed here. Once the exothermic reaction had subsided, the mixture was heated to 90° C. for a further 3 hours and the methanol formed and ethanol present were distilled off via a bridge at a bottoms temperature of up to 139° C.

To the residue thus obtained was added 1258 g (4.55 mol) of i-octyltriethoxysilane (=2,4,4-trimethylpentyltriethoxysilane) and the mixture was heated to 240° C., with the ethanol formed distilled off via a bridge. The reaction time was 12 hours. On cooling, TBD crystallized out of the bottoms. Addition of 440 g of ethanol afforded an almost colorless, homogeneous TBD solution (total weight 1880 g) having a TBD content of 19% by weight (387 g TBD, HPLC analysis), corresponding to a TBD yield of 90%.

Example 2

203 g (1.55 mol) of bis(3-aminopropyl)amine was heated to 60° C. and 146 g (1.62 mol) of dimethyl carbonate was added over a period of one hour, with stirring. A temperature rise in bottoms temperature to 86° C. was observed here. The mixture was heated to 90° C. for a further 3 hours and the methanol formed was then distilled off.

To the residue thus obtained was added 624 g (2.26 mol) of isooctyltriethoxysilane and the mixture was heated to 250° C., with stirring, with the ethanol formed distilled off via a bridge. The reaction time at 250° C. was 9 hours. On cooling, TBD crystallized out of the bottoms. Addition of 210 g of ethanol afforded an almost colorless, homogeneous TBD solution (total weight 940 g) having a TBD content of 20% by weight (188 g TBD, HPLC analysis), corresponding to a TBD yield of 87%.

Comparative Example 3

To 77.3 g (0.59 mol) of bis(3-aminopropyl)amine was added 55.6 g (0.62 mol) of dimethyl carbonate at room temperature over a period of one hour, with stirring. A temperature rise in bottoms temperature to 50° C. was observed here. The mixture was heated to 90° C. for a further 3 hours and the methanol formed was then distilled off. 109 g of residue was obtained, to which was added 232 g of a mixture consisting of 25% tetraethoxysilane, 35% hexaethoxydisiloxane, 26% octaethoxytrisiloxane, 10% octaethoxycyclotetrasiloxane, and 4% decaethoxytetrasiloxane and the mixture was heated, with stirring, to temperatures between 210° C. and 235° C. for 10 hours, with removal of ethanol by distillation. After cooling, the three-phase (two liquid phases and solid) dark-colored reaction mixture containing the crystalline TBD was mixed with 60 g of ethanol. The lower viscous phase initially persisted and dissolved after heating to 70° C. for 10 hours. The homogeneous solution obtained (total weight 275 g) had a TBD content (HPLC) of 10.4%, corresponding to 28.6 g of TBD (35%).

Example 4

To 109 g of the product from the reaction of bis(3-aminopropyl)amine with dimethyl carbonate according to Example 2 was added 251 g of an alkoxysilane mixture consisting of 30% diethoxydi(2-butoxy)silane, 50% ethoxytri(2-butoxy)silane and 20% tetra(2-butoxy)silane and the mixture was heated, with stirring, to temperatures between 210° C. and 235° C. for 10 hours, with removal of ethanol and 2-butanol by distillation. After cooling, the reaction mixture containing crystalline TBD was mixed with 43 g of ethanol. A homogeneous solution formed (total weight 386 g), the TBD content (HPLC) was 22.4%, corresponding to 86.5 g of TBD (90%).

Example 5

30.0 g (0.29 mol) of diethylenetriamine was heated to 50° C. and 21.8 g (0.24 mol) of dimethyl carbonate was added over a period of 45 minutes, with stirring. A temperature rise in bottoms temperature to 50° C. was observed here. The mixture was heated to 90° C. for a further 3 hours, after which the methanol formed was distilled off at a bottoms temperature between 125-145° C. 40.2 g of residue was obtained, to which was added 200 g of i-octyltriethoxysilane and the mixture was heated, with stirring, to 220° C. to 250° C. for 20 hours. The ethanol thereby formed was removed by distillation. Once the reaction mixture had cooled, 38 g of ethanol was added. A clear homogeneous solution with a TBO content of 6.1% (HPLC) was obtained.

Example 6

To 117 g of the product from the reaction of bis(3-aminopropyl)amine with dimethyl carbonate according to Example 2 was added 300 g of i-octyltriethoxysilane and the mixture was heated, with stirring, to temperatures between 230 and 250° C., with the ethanol formed (49 g) distilled off via a bridge. The reaction time was 13 hours. The mixture was then cooled to approx. 190° C. and a sample of the reaction mixture, which was homogeneous at this temperature, was investigated by HPLC. The TBD content was 23%. This corresponds to 85 g of TBD (99%). On cooling to ambient temperature, TBD crystallized out of the bottoms. Addition of 71 g of ethanol afforded an almost colorless, homogeneous TBD solution.

Example 7

To 204 g (1.55 mol) of bis(3-aminopropyl)amine was added 14.4 g of the TBD solution obtained according to Example 1, the mixture was heated to 90° C., and 191 g (1.62 mol) of diethyl carbonate was added over a period of one hour, with stirring. A temperature rise in bottoms temperature to 102° C. was observed here. The mixture was heated to 105° C. for a further 3 hours (ethanol reflux), after which the ethanol formed (142 g) was distilled off at standard pressure and at a bottoms temperature of 110 to 160° C. 271 g of residue was obtained (content of cyclic urea 90%). To 117 g (0.67 mmol) of the residue was added 248 g of i-octyltriethoxysilane and the mixture was heated, with stirring, to 245° C., with the ethanol formed distilled off via a bridge. The reaction time at 245° C. was 12 hours. On cooling to ambient temperature, TBD crystallized out of the bottoms. Addition of 87 g of ethanol afforded a homogeneous TBD solution (total weight 367 g) having a TBD content of 18% by weight (66 g TBD, HPLC analysis), corresponding to a TBD yield of 72%.

Example 8

To 103 g (0.78 mol) of bis(3-aminopropyl)amine was added 7.2 g of the TBD solution obtained according to Example 1 and 100 g of i-octyltriethoxysilane, the mixture was heated to 90° C., and 95.5 g (0.80 mol) of diethyl carbonate was added over a period of one hour, with stirring. A temperature rise in bottoms temperature to 106° C. was observed here. The mixture was heated to 105° C. for a further 3 hours (ethanol reflux), after which the ethanol formed (73 g) was distilled off at standard pressure and at a bottoms temperature of 110 to 160° C. 233 g of a two-phase residue was obtained. To this was added 182 g of i-octyltriethoxysilane and the mixture was heated, with stirring, to 245° C., with the ethanol formed (approx. 70 g) distilled off via a bridge. The reaction time at 245° C. was 12 hours. On cooling to ambient temperature, TBD crystallized out of the bottoms. Addition of 100 g of ethanol afforded a homogeneous TBD solution (total weight 445 g) having a TBD content of 22% by weight (98 g TBD, HPLC analysis), corresponding to a TBD yield of 91%.

The invention claimed is:

1. A process for producing bicyclic guanidines, comprising reacting (A) dialkylenetriamine with (B) dialkyl carbonate in the presence of (C) silane of the formula $$Si(OR^x)_o R^y_{(4-o)} \quad (IV)$$

and/or partial hydrolysates thereof,
where
$R^x$ are identical or different and are monovalent hydrocarbon radicals having 2 to 10 carbon atoms,
$R^y$ are identical or different and are monovalent hydrocarbon radicals having 1 to 30 carbon atoms in which individual $CH_2$ moieties not bonded to silicon are optionally replaced by oxygen or substituted by silyl group(s) and
is 1, 2, 3 or 4,
with the proviso that, in the case of silanes of the formula (IV) where o=4, at least two radicals $R^x$ represent a monovalent, optionally substituted hydrocarbon radical having 3 to 10 carbon atoms.

2. The process of claim 1, wherein the dialkylenetriamines (A) have the formula $$H_2N-(CR^a_2)_m-CR^a_2-NH-CR^a_2-(CR^a_2)_n-NH_2 \quad (II)$$

where
m and n are independently 1, 2, 3 or 4 and
$R^a$ are each identical or different and are hydrogen or a monovalent hydrocarbon radical in which individual methylene groups are optionally replaced by oxygen or by —NH— or —NR$^d$— moieties, where $R^d$ represents monovalent hydrocarbon radicals having 2 to 10 carbon atoms.

3. The process of claim 1, wherein the dialkyl carbonates (B) are of the formula $$R^b O-CO-OR^b \quad (III)$$

where
$R^b$ each are identical or different and are mono- or divalent, aliphatically saturated hydrocarbon radicals having from 1 to 10 carbon atoms.

4. The process of claim 1, wherein component (C) is used in amounts of 30 to 1000 parts by weight based on 100 parts by weight of dialkylenetriamine (A).

5. The process of claim 1, wherein components comprising (A) and (B), and optionally a nitrogen base (D) different from (A) are mixed and allowed to react in a first step, optionally in the presence of solvents (E), fillers (f), colorants (g), and/or polymers (h), which is followed by a second step in which component (C) and optionally components (D), (E), (f), (g) and (h) are added and the mixture is heated to a temperature greater than 200° C.

6. A bicyclic guanidine-containing preparation, comprising
(a) bicyclic guanidine(s),
(b) silane(s) of the formula, $$Si(OR^x)_o R^y_{(4-o)} \quad (IV)$$

and/or partial hydrolysates thereof,
where
$R^x$ are identical or different and are monovalent hydrocarbon radicals having 2 to 10 carbon atoms, $R^y$ are identical or different and are monovalent hydrocarbon radicals having 1 to 30 carbon atoms in which individual $CH_2$ moieties not bonded to silicon are optionally replaced by oxygen or substituted by silyl group(s) and o is 1, 2, 3 or 4, with the proviso that, in the case of silanes of the formula (IV) where o=4, at least two radicals $R^x$ represent a monovalent, optionally substituted hydrocarbon radical having 3 to 10 carbon atoms, (c) compound(s) $R^cOH$, wherein $R^c$ is hydrogen or a monovalent hydrocarbon radical having 1 to 30 carbon atoms optionally interrupted by oxygen, or a hydrocarbon radical substituted by hydroxyl groups, optionally (e) organic solvents free of hydroxyl groups attached to aliphatic carbon atoms, optionally (f) fillers, optionally (g) colorants, and optionally (h) polymers.

7. The preparation of claim 6, wherein the content of bicyclic guanidines (a) is 2% to 35% by weight.

8. The preparation of claim 6, wherein the content of silanes and/or siloxanes (b) is 20% to 90% by weight.

9. A process for producing a preparation of claim 6, comprising mixing the individual components in any desired order.

10. A process for producing bicyclic guanidines, comprising reacting (A) dialkylenetriamine with (B) dialkyl carbonate in the presence of (C) silane of the formula $$Si(OR^x)_o R^y_{(4-o)} \quad (IV)$$

and/or partial hydrolysates thereof, where $R^x$ are identical or different and are monovalent hydrocarbon radicals having 2 to 10 carbon atoms, $R^y$ are identical or different and are monovalent hydrocarbon radicals having 1 to 30 carbon atoms in which individual $CH_2$ moieties not bonded to silicon are optionally replaced by oxygen or substituted by silyl group(s) and is 1, 2, or 3.

11. The process of claim 10, wherein $R^y$ is a hydrocarbon radical having from 1-12 carbon atoms.

12. The process of claim 10, wherein at least one silane (C) is selected from the group consisting of i-octyl-Si(OEt)$_3$, methyltriethoxysilane, ethyltriethoxysilane, vinyltriethoxysilane, propyltriethoxysilane, butyltriethoxysilane, cyclohexyltriethoxysilane, 2-methylpropyltriethoxysilane, pentyltriethoxysilane, methyltris(1-methylethoxy)silane, n-octyltriethoxysilane, phenyltriethoxysilane, benzyltriethoxysilane, (EtO)$_3$Si—CH$_2$—CH$_2$—Si(OEt)$_3$, (EtO)$_3$Si—CH$_2$—CH$_2$—SiMe$_3$, (EtO)$_2$MeSi—CH$_2$—CH$_2$—SiMe(OEt)$_2$, and partial hydrolysates thereof.

13. The process of claim 10, wherein at least one silane (C) is i-octyltriethoxysilane.

\* \* \* \* \*

UNITED STATES PATENT AND TRADEMARK OFFICE
CERTIFICATE OF CORRECTION

| | | |
|---|---|---|
| PATENT NO. | : 12,145,937 B2 | Page 1 of 1 |
| APPLICATION NO. | : 17/272898 | |
| DATED | : November 19, 2024 | |
| INVENTOR(S) | : Elke Fritz-Langhals et al. | |

It is certified that error appears in the above-identified patent and that said Letters Patent is hereby corrected as shown below:

In the Claims

Column 12, Lines 20-21, Claim 1:
After "substituted by silyl group(s) and"
Delete "is 1, 2, 3, or 4" and
Insert -- o is 1, 2, 3, or 4 --.

Signed and Sealed this
Thirtieth Day of September, 2025

John A. Squires
*Director of the United States Patent and Trademark Office*